United States Patent [19]

Hercelin et al.

[11] Patent Number: 4,478,819
[45] Date of Patent: Oct. 23, 1984

[54] NOVEL ORAL PREPARATIONS

[75] Inventors: Bernard Hercelin, Clermont; Irene Mary, Le Plessis-Bouchard; Vien N. Nung, Elisabethville, all of France

[73] Assignee: Roussel Rclaf, Paris, France

[21] Appl. No.: 488,683

[22] Filed: Apr. 26, 1983

[30] Foreign Application Priority Data

Apr. 26, 1982 [FR] France ................................ 82 07137

[51] Int. Cl.$^3$ .......................... A61K 9/48; A61K 9/28
[52] U.S. Cl. ...................................... 424/37; 424/274
[58] Field of Search ........................... 424/44, 37, 274

[56] References Cited

U.S. PATENT DOCUMENTS

| | | | |
|---|---|---|---|
| 2,211,485 | 8/1940 | Zimmerman | 424/44 |
| 2,540,253 | 2/1951 | Gakenheimer | 424/44 |
| 2,999,293 | 9/1961 | Taff et al. | 424/44 |
| 3,131,123 | 4/1964 | Masquelier | 424/44 |
| 3,136,692 | 6/1964 | Bandelin | 424/44 |
| 3,495,001 | 2/1970 | Leonards | 424/44 |
| 3,676,549 | 7/1972 | Higuchi et al. | 424/44 |
| 3,764,668 | 10/1973 | Higuchi et al. | 424/44 |
| 3,856,967 | 12/1974 | Allais et al. | 424/274 |
| 3,882,228 | 5/1975 | Boncey et al. | 424/44 |
| 3,944,660 | 3/1976 | Gottfried et al. | 424/44 |
| 4,265,847 | 5/1981 | Hunt et al. | 424/44 |
| 4,265,874 | 5/1981 | Bonsen et al. | 424/44 |
| 4,344,929 | 8/1982 | Bonsen et al. | 424/44 |

FOREIGN PATENT DOCUMENTS

| | | |
|---|---|---|
| 0077047 | 4/1983 | European Pat. Off. |
| 7337M | 11/1969 | France |
| 51-35415 | 3/1976 | Japan |
| 1260868 | 1/1972 | United Kingdom |

OTHER PUBLICATIONS

Mary et al, CA. 98: 83210r (1983) of J. Pharm. Belg. 1982 37(6): 418–421, Studies on Clometacin Part III, Correlation Plasma Levels Analgesic Activity-Mice.
Van Cantfort et al., CA. 98 83209x, (1983) of J. Pharm. Belg. 1982 37(6) 410–417, Studies on Clometacin Part II. Metabolism Bioavailability in the Monkey and in Man.
Van Canfort et al., CA. 98 100717F (1983) of J. Pharm. Belg. 1982 37(6) 401–409, Studies on Clometacin, Part I. Metabolism Bioavailability Clomethacin in the Rat.
Deraedt et al. CA. 86: 133507x (1977) of Arch. Inf. Pharmacodyn. Ther. (976 224(1): 30–42, Inhibition of Prostaglandin Biosynthesis by Non-Narcotic Analgesic Drugs.
Toguch et al. CA. 85: 51748w (1976) of Japan Kokai 76 35415, 25 Mar. 1976, Production of Solid Tablets.
Allais et al. CA. 88: 131402u (1975) of Eur. Med. Chem.-Chim. Ther. 1975 10(2): 187–194, Non-Narcotic Analgesic and Anti-Inflammatory Agents. 1-Carboxyalkyl-3-Acylindoles.
Doebel et al. CA. 78: 11439m (1972) of J. Med. Chem. 1972 15(10):1081–1082, Derivatives of Indole-1-Acetic Acid as Anti-Inflammatory Agents.
Allais et al. CA. 72:43440x (1970) of Ger. Offen. 1,901,167 11 Dec. 1969, 1-(Carboxyalkyl)-2-Methyl-3[-Substituted Benzoyl]-Indoles.

*Primary Examiner*—Shep K. Rose
*Attorney, Agent, or Firm*—Charles A. Muserlian

[57] ABSTRACT

A novel oral pharmaceutical composition comprising extrusion granules of a mixture comprised of 50 to 70% by weight of clometacine, 5 to 20% by weight of an alkali metal carbonate and an anhydrous excipient for non aqueous granulation having a rapid action and a very strong increased total biodisponibility and a method of relieving pain in warm-blooded animals.

12 Claims, No Drawings ary properties such as to serve as a binder. Examples of such diluents are starch and its derivatives, lactose, mannitol and preferably celluloses such as microcrystalline cellulose such as Avicel PH 101. The microcrystalline celluloses, for example, ameliorate equally the malleability of the powder mixture. They are usually used in proportions of 5 to 40% by weight, preferably about 20% by weight, of the mixture.

NOVEL ORAL PREPARATIONS

STATE OF THE ART

In the field of antalgesics, it is particularly interesting to have medicaments having a very rapid onset of activity to obtain early relief from pain, Clometacine or 3-(4-chlorobenzoyl)-6-methoxy-2-methylindolo-1-acetic acid is described as an antalgic in French patent BSM No. 7337 but the usual tablet forms are rather slow in their onset of activity. It is known that the intensity and the regularity of absorption of oral compositions can be increased by increasing their status of division, i.e. making the particles smaller. It is also know to use local modifications of pH to increase their absorption such as by adding a basic adjuvant to the active acid ingredient.

OBJECTS OF THE INVENTION

It is an object of the invention to provide oral antalgic compositions containing clometacine as the active ingredient having a rapid onset of activity, large biodisponibility and good regularity of absorption.

It is an object of the invention to provide an improved method of relieving pain in warm-blooded animals.

These and other objects and advantages of the invention will become obvious from the following detailed description.

THE INVENTION

The novel oral pharmaceutical compositions of the invention are comprised of extrusion granules of a mixture comprised of 50 to 70% by weight of clometacine, 5 to 20% by weight of an alkali metal carbonate and an anhydrous excipient for non aqueous granulation. The compositions for the first time increases the degree of divisions of the classical granule preparations.

Classical granules have been prepared with an alkali metal carbonate as basic adjuvant. In the divided forms, no improvement was noted with respect to the reference tablet form.

The applicants prepared granules by extrusion and such granules may be prepared without an adjuvant, then with basic adjuvants such as triethanolamine and dipotassium phosphate. No improvement of the resorption rate or the biodisponibility of clometacine is seen with these forms. The applicant then prepared by extrusion granules containing an alkali metal carbonate as basic adjuvant and it was determined that surprisingly the granules showed a rapid action and a very greatly increased total biodisponibility.

The alkali metal carbonate may be sodium or potassium carbonate with the latter being preferred. The active principle for the preparation of the clometacine granules requires a granulation excipient to form solid aggregates of particles of active principle. The granulation excipient is preferably comprised of at least one adjuvant selected from the group consisting of diluents, lubricants, binders and disintegrating agents.

The diluents serve to increase the volume of the powdered mass to be treated and it is capable of increasing the malleability of the mass and possesses other secondary properties such as to serve as a binder. Examples of such diluents are starch and its derivatives, lactose, mannitol and preferably celluloses such as microcrystalline cellulose such as Avicel PH 101. The microcrystalline celluloses, for example, ameliorate equally the malleability of the powder mixture. They are usually used in proportions of 5 to 40% by weight, preferably about 20% by weight, of the mixture.

The binders permit the agglomeration of the powder particles among themselves and examples of suitable binders are cellulose derivatives such as methylcellulose, starch and its derivatives and preferably polyoxyethyleneglycols of low or average molecular weight (equal to or less than 8000), especially PEG 6000 which may serve both as a binder and a lubricant. The binders preferably are 1 to 10% by weight, most preferably about 5% by weight of the granules.

The disintegrating agents permit or ameliorate the disintegration of the granules when they have been injested by the patient and examples of suitable disintegrating agents are water soluble products selected from diluents like saccharose or lactose as well as products capable of swelling in aqueous media such as starch and its derivatives and preferably powdered silica or microcrystalline cellulose. When the products have as their essential function a disintegrating activity, they are used in less than 3% by weight of the composition, preferably about 1% by weight. When the products are to function as both disintegrating agent and diluent such as in the case of microcrystalline cellulose, the amount may be as high as 40% by weight, preferably 10 to 25% by weight, of the granules.

The lubricants ameliorate the malleability of the mass to be worked and permit a good homogenity of the powder mass. Examples of suitable lubricants are talc, magnesium stearate and other stearates, glycerol esters such as precirol (palmito stearate of glycerol) and preferably polyoxyethylene glycols of average or high molecular weight (i.e. equal to or greater than 6000) and hydroxypropylmethylcellulose. The lubricants are used in amounts of less than 10% by weight, preferably about 5% by weight, of the granules. The choice is important for the granulation yields of the extrusion.

The granulation of the products of the invention is effected in a known fashion by admixing the adjuvants making up the excipient with clometacine and alkali metal carbonate, wetting the mixture with an anhydrous solvent such as methylene chloride or preferably a lower alkanol such as isopropanol or methanol or most preferably ethanol to form a paste, extruding the paste through a drawing plate into filaments, breaking the filaments into granules and drying the same.

The mixing can be effected in known mixers such as drum mixers or planetory mixers or screw mixers for example. The wetting of the dry powder is sufficient to obtain a pasty mixture which can be extruded and an example is 2.5 to 3 liters of solvent for a charge of 5 kg of powder.

The paste extrusion is effected to obtain multiple filaments provided by a grill whose pore diameter is preferably 0.6 to 1.2 mm and an example of a suitable extruder is that of Fuji Paudal extruder. The filaments coming out of the extruder pores are broken into microcylinders and advantageously made spherical, especially if it is desired to coat them, for example with the Marumerizer Fuji-Paudal apparatus.

The dried granules are most advantageously coated to protect the active ingredient and the coating should be sufficiently thin not to effect the rapidity of absorption. The coating is preferably effected with a gel film such as an acrylic derivative, polyoxyethyleneglycol of a high molecular weight or preferably a cellulose derivative, especially ethylcellulose. The coating cover is about not more than 2% by weight of the coated granules and is preferably about 1% by weight of the coated granules.

Given the thinness of the coating, the coating advantageous contains at least one plasticizer and examples of suitable plasticizers are propyleneglycol, diethyl phthalate, dibutyl phthalate and preferably butyl phthalate as well as partial esters of fatty acids and hexitol anhydrides such as monolaurate or preferably monostearate of sorbitol anhydride. The coating may be applied in a turbine or in suspension for example and may be colored if desired.

The granules may be in the form of multiple doses or individual doses, in gelules (capsules) or cachets.

The process of the invention for the preparation of the oral pharmaceutical compositions of the invention comprises forming an intimate mixture of 50 to 70% by weight of clometacine, 5 to 20% by weight of an alkali metal carbonate and an anhydrous excipient for non aqueous granulation progressively wetting the mixture with an anhydrous solvent to obtain a paste, extruding the paste into filaments through a drawing plate, rupturing the filaments into microcylinders drying the microcylinders, and optionally coating them and conditioning them into an usual pharmaceutical form for microgranules. In a preferred mode of the process of the invention, the microcylinders are rendered substantially spherical and the microspheres are coated.

The novel method of the invention for relieving pain in warm-blooded animals, including humans, comprises orally administrating to humans an analgesically effective amount of a composition of extrusion granules of a mixture comprised of 50 to 70% by weight of clometacine, 5 to 20% by weight of an alkali metal carbonate and an anhydrous excipient for non aqueous granulation. The usual effective amount is 1 to 45 mg/kg.

In a study conducted on dogs, the granules of the invention were compared with the commercial tablet formulation containing 150 mg of clometacine as a reference and the product of the invention showed a gain in early absorptions estimated by the difference of hourly values of concentration peaks of 1.5 to 2.5 hours, a strong increase in total absorption of clometacine since this total absorption, estimated by the surfaces under the curves of plasmatic concentrations between 0 and 8 hours, is multiplied by about 4.5 as compared to comparable administered dose of clometacine and a very great regularity of blood levels of clometacine in the animals. The advantages of the granules is suppressed if they are compressed into tablets.

In the following examples there are described several preferred embodiments to illustrate the invention. However, it should be understood that the invention is not intended to be limited to the specific embodiments.

EXAMPLE 1

Gelules containing coated spherical granules obtained by extrusion

An intimate dry mixture of 2,985 g of clometacine, 576 g of potassium carbonate, 904 g of microcrystalline cellulose (Avicel PH 101), 48 g of powdered silica (aerosil 200), 239 g of hydroxypropyl methylcellulose (Pharmacoat 606) and 248 g of polyoxyethylene glycol 6000 (PEG 6000) was made and then was progressively wetted with 3 liters of absolute alcohol. The resulting dough was extruded through a Fuji-Pandel extruder with a pore diameter of 0.8 mm and the filaments were broken into microcylinders and made spherical with a Marumerizer apparatus of Fuji-Pandal and was dried. The dried granules were coated with a solution of 60 g of ethylcellulose, 12 g of butyl phthalate and 3 g of monostearate of anhydrous sorbitol (Arlacel 60) in a 1-1 ethanol-methylene chloride mixture and the coated granules were filled into gelules to contain 100,000 mg of clometacine per gelule.

EXAMPLE 2

The procedure of Example 1 was repeated to obtain coated spherical granules containing a mixture of 150 mg of clometacine, 57.5 mg of Avicel PH 101, 2.50 mg of Aerosil 200, 12.50 mg of PEG 6000 and 29.00 mg of potassium carbonate. The coating solution was 3.00 mg of ethyl cellulose, 0.75 mg of butyl phthalate and 0.25 mg of Arlacel 60 per gelule.

PHARMACEUTICAL DATA

Test A: The test was effected on male and female Charles River macaco(cynomolgus) weighing 3 to 3.4 kg and clometacine was orally administered in the form of tablets or gelules containing prior art granules or the extruded granules of the invention. The clometacine in the blood was determined by samples from the femoral vein at 30 minutes, 1,2,3,4,6 and 8 hours after administration and the average plasmatic levels of $\mu$g of clometacine per ml are reported in Table I.

The forms administered were the classical tablet sold in France (form A), classical granules (form B), extruded granule (form C), extruded granulate with 62.5 mg of triethanolamine adjuvant (form D), extruded granulate with 146.0 mg of dipotassium acid phosphate adjuvant (form E), extruded granulate with 29.0 mg of potassium carbonate granule adjuvant (form F) and extruded granulate with 29.0 mg of potassium carbonate tablet adjuvant (form G). The granules contained 150.00 mg of clometacine, 57.50 mg of Avicel PH 101, 2.50 mg of Aerosil 200, 12.50 mg of PEG 6000 and possibly the indicated adjuvant. The coating consisted of 3.0 mg of ethyl cellulose, 0.75 mg of butyl phthalate and 0.25 mg of Aracel 60.

TABLE I

| Administered Form | Time of Sample in hours | | | | | | |
|---|---|---|---|---|---|---|---|
| | 0.5 | 1 | 2 | 3 | 4 | 6 | 8 |
| A | — | 0 | 0,3 | 0,4 | 1,0 | 8,0 | 24,1 |
| B | — | 0,4 | 0,9 | 2,7 | 6,5 | 9,1 | 10,5 |
| C | — | 0,65 | 0,65 | 2,7 | 6,4 | 7,9 | 10,5 |
| D | 0,7 | 2,8 | 4,7 | 5,3 | 5,8 | 23,8 | 25,6 |
| E | 2,0 | 3,8 | 5,6 | 7.0 | 10,2 | 21,3 | 12,1 |
| F | — | 15,8 | 20,9 | 19,5 | 19,0 | 14,2 | 6,3 |
| G | 1,7 | 3,5 | 5,3 | 5,4 | 4,8 | 24,1 | 25 |

The results of Table I show that form F which are extruded granules with potassium carbonate as the adjuvant shows a rapid very good appearance in comparison to the other forms by the important blood level of clometacine which is obtained quickly and for a prolonged duration.

Test B: This test was effected on groups of 4 Beagle dogs about 12 to 14 months old and weighing about 11 kg for the females and 12.5 kg for the males with equal amount of each sex in the groups. Blood samples were taken from the median subcutaneous vein in the front paw at different times after the administration to determine the blood level of clometacine and the results are expressed in $\mu$g of clometacine per ml of blood in Table II.

The forms tested contained 150 mg of clometacine and were classical tablets sold in France (form A), classical granules with 29.0 mg of potassium carbonate adjuvant (form H) and extruded granules with 29.0 mg of potassium carbonate adjuvant (forms I and J-2 different lots) with the granules having the composition indicated in Test A.

TABLE II

| Administered form | Time of samples in hours | | | | | | |
|---|---|---|---|---|---|---|---|
| | 0.5 | 1 | 2 | 3 | 4 | 6 | 8 |
| A | 0 | 0,5 | 1,5 | 2,7 | 1,6 | 1,0 | 0,5 |
| H | 0,8 | 1,3 | 9,5 | 5,3 | 4,1 | 3,4 | 2,2 |
| I | 4,5 | 5,2 | 4,8 | 5,0 | 6,5 | 6,2 | 2,6 |
| J | 1,7 | 5,3 | 7,1 | 9,8 | 8,7 | 5,4 | 2,9 |

It can be seen from Table II that forms I and J which are extruded granules with potassium carbonate adjuvant show rapid very good appearance as compared to the other forms as seen by the quick and prolonged level of clometacine in the blood.

Test C: To show the strong increase in blood levels resulting from the new form of clometacine of the invention, extruded granules containing 100 mg of the active material were prepared and used in random crossed tests with groups of 10 dogs. The classical French tablets (form A) containing 150 mg of clometacine were compared with extruded granules (forms K and L) containing 100.00 mg of clometacine, 19.30 mg of potassium carbonate, 30.30 mg of Avicel PH 101, 8.00 mg of Pharmacoat 606, 1.60 mg of Aerosil 200 and 8.30 mg of PEG 6000 and the coating was 2.00 mg of ethyl cellulose, 0.40 mg of butyl phthalate and 0.10 mg of Arlacel 60.

The average plasmatic levels expressed in $\mu$g of clometacine per ml as well as the total absorption of the active ingredient in 8 hours estimated by measuring the surfaces of curves (SSC) from 0 to 8 hours expressed in $\mu g \cdot h \cdot ml^{-1}$ are reported in Table III.

TABLE III

| Administered Form (dose of clometacine) | Time of Sample in hours | | | | | | | | Average SSC |
|---|---|---|---|---|---|---|---|---|---|
| | 0.5 | 1 | 1.5 | 2 | 3 | 4 | 6 | 8 | |
| A (150 mg) | — | — | 0,2 ± 0,35 | 0,5 ± 0,6 | 0,6 ± 0,8 | 0,55 ± 0,55 | 0,7 ± 0,6 | 0,6 ± 0,8 | 4,0 ± 2,8 |
| K (100 mg) | 1,4 ± 2,3 | 1,85 ± 1,4 | 2,0 ± 1,5 | 2,2 ± 1,7 | 2,3 ± 2 | 2,2 ± 1,7 | 1,1 ± 1,0 | 1,0 ± 0,9 | 13,5 ± 7,6 |
| L ((100 mg) | 1,45 ± 1,2 | 1,45 ± 1,2 | 2,1 ± 1,7 | 2,2 ± 1,2 | 2,2 ± 1,6 | 2,05 ± 1,7 | 2,0 ± 1,8 | 0,8 ± 0,7 | 13,0 ± 6,1 |

Table III shows that the total absorption estimated by SSC is about 3 times greater for the extruded granules with potassium carbonate adjuvant as compared to the known tablets containing 150 mg of clometacine and is 4.5 times greater based on equal amounts of clometacine.

The peaks of concentration (C) of clometacine in the blood were also determined in the test and the results are reported in Table IV.

TABLE IV

| Administration form (dose of clometacine) | Average max. concentration in ug/ml | Average max. time in hours |
|---|---|---|
| A (150 mg) | 1,2 ± 0,9 | 4,9 ± 2,2 |
| K (100 mg) | 3,85 ± 2 | 2,4 ± 1,5 |
| L (100 mg) | 3,9 ± 1,3 | 2,4 ± 1,7 |

Table IV shows a strong increase in clometecine maximum concentration in the blood for the claimed granules as compared to the tablets as well as an important early onset of activity. Finally, the lessening of the coefficients of variation calculated from the average SSC and the average maximum concentration show a gain in regularity of absorption in dogs as compared to the known tablets.

Various modifications of the compositions and method of the invention may be made without departing from the spirit or scope thereof and it is to be understood that the invention is intended to be limited only as defined in the appended claims.

What we claim is:

1. An oral pharmaceutical rapid onset capsule, gelule or cachet composition containing an analgesically effective amount of clometacine in the form of extrusion granules whose rapid onset advantages are suppressed if they are compressed into tablets and comprising a mixture comprised of 50 to 70% by weight of clometacine, 5 to 20% by weight of an alkali metal carbonate and an anhydrous excipient for non aqueous granulation.

2. A composition of claim 1 wherein the granules contain 58 to 60% by weight of clometacine and 9.5 to 13% by weight of alkali metal carbonate.

3. A composition of claim 1 containing the granulation excipient constituted of adjuvants selected from the group consisting of diluents, lubricants, binders and disintegrating agents.

4. A composition of claim 1 containing microcrystalline cellulose as a diluent.

5. A composition of claim 1 containing a polyoxyethylene glycol of low or average molecular weight as a binder.

6. A composition of claim 1 containing a lubricating agent selected from the group consisting of polyoxyethylene glycol of average or high molecular weight and hydroxypropylmethyl cellulose.

7. A composition of claim 1 containing a disintegrating agent selected from the group consisting of powdered silica and microcrystalline cellulose.

8. A composition of claim 1 wherein the alkali metal carbonate is potassium carbonate.

9. A composition of claim 1 wherein the granules are placed in capsules.

10. A method of relieving pain in warm-blooded animals comprising administering to warm-blooded animals an analgesically effective amount of a capsule, gelule, or cachet composition of claim 1.

11. A method of claim 10 wherein the granules contain 58 to 60% by weight of clometacine and 9.5 to 13% by weight of alkali metal carbonate.

12. A method of claim 10 containing the granulation excipient constituted of adjuvants selected from the group consisting of diluents, lubricants, binders and disintegrating agents.

* * * * *